(12) United States Patent
Marumori et al.

(10) Patent No.: US 9,283,058 B2
(45) Date of Patent: *Mar. 15, 2016

(54) IMPRESSION TRAY FOR LOCAL AREA

(71) Applicant: GC CORPORATION, Tokyo (JP)

(72) Inventors: Hidefumi Marumori, Yokohama (JP); Hiroshi Kamohara, Matsudo (JP)

(73) Assignee: GC CORPORATION, Tokyo (JP)

( * ) Notice: Subject to any disclaimer, the term of this patent is extended or adjusted under 35 U.S.C. 154(b) by 93 days.

This patent is subject to a terminal disclaimer.

(21) Appl. No.: 13/853,420

(22) Filed: Mar. 29, 2013

(65) Prior Publication Data

US 2013/0260330 A1  Oct. 3, 2013

(30) Foreign Application Priority Data

Mar. 30, 2012 (JP) ................................. 2012-080307

(51) Int. Cl.
*A61C 9/00* (2006.01)

(52) U.S. Cl.
CPC .................................. *A61C 9/0006* (2013.01)

(58) Field of Classification Search
CPC .... A61C 9/0006; A61C 9/00; A61C 13/0004; A61C 19/05; A61C 19/005; A61C 19/006; A61C 19/066
USPC .................................... 433/34, 36, 37, 45–48
See application file for complete search history.

(56) References Cited

U.S. PATENT DOCUMENTS

| | | | |
|---|---|---|---|
| 2,758,374 A | | 8/1956 | Fisher et al. |
| 3,473,225 A | * | 10/1969 | Walker et al. .................... 433/48 |
| 5,076,785 A | * | 12/1991 | Tsai ................................ 433/46 |
| 5,336,086 A | * | 8/1994 | Simmen et al. .................. 433/37 |
| 5,752,826 A | | 5/1998 | Andreiko |
| 7,273,371 B2 | * | 9/2007 | Massad ............................ 433/37 |
| D686,733 S | * | 7/2013 | Marumori et al. ............ D24/181 |
| 2005/0106529 A1 | * | 5/2005 | Abolfathi et al. ............... 433/41 |

FOREIGN PATENT DOCUMENTS

| | | |
|---|---|---|
| JP | 2000-135227 A | 5/2000 |
| JP | 2013-75092 A | 4/2013 |

OTHER PUBLICATIONS

U.S. Appl. No. 13/853,482, filed Mar. 29, 2013, Marumori, et al.
U.S. Appl. No. 13/782,397, filed Mar. 1, 2013, Marumori, et al.
U.S. Appl. No. 29/425,723, filed Jun. 26, 2012, Marumori, et al.
U.S. Appl. No. 29/425,716, filed Jun. 26, 2012, Marumori, et al.
U.S. Appl. No. 29/425,712, filed Jun. 26, 2012, Marumori, et al.
Extended European Search Report issued Jun. 28, 2013 in Patent Application No. 13001611.6.

* cited by examiner

*Primary Examiner* — Yogesh Patel
(74) *Attorney, Agent, or Firm* — Oblon, McClelland, Maier & Neustadt, L.L.P.

(57) ABSTRACT

The invention provides a plastic impression tray for a local area having an outer wall provided in an outer side of a curve of a bottom portion, and an inner wall provided in an inner side of the curve of the bottom portion. A rim having a particular height is provided in the bottom portion side along each of upper ends of the outer wall and the inner wall, elongated through holes each reaching the bottom portion from a portion just below the rim are formed approximately at uniform distances in the outer wall and the inner wall, circular through holes each having a particular diameter are formed at particular positions in the bottom portion, and elongated end portion side through holes each having a particular width and a particular length are provided vertically to an axial direction of the bottom portion, in both ends of the bottom portion.

7 Claims, 3 Drawing Sheets

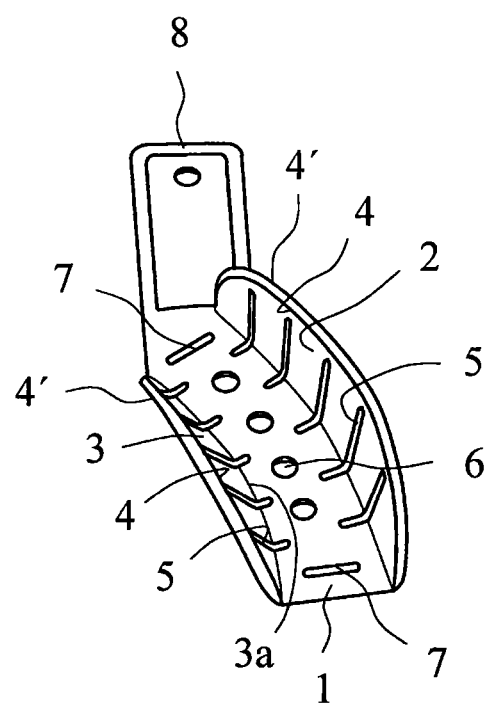

IMPRESSION TRAY FOR LOCAL AREA

CROSS REFERENCE TO RELATED APPLICATION

This application claims priority to Japanese Patent Application No. 2012-080307, filed Mar. 30, 2012, the text of which is incorporated herein by reference.

BACKGROUND OF THE INVENTION

1. Field of the Invention

The present invention relates to a plastic impression tray for a local area to be used for taking an impression of a local area within an oral cavity as a preparation stage of producing a partial denture, a bridge, an inlay or the like as a prosthetic appliance in dentistry, wherein the impression tray for a local area can prevent a set impression material from floating upward from the tray and being peeled off from the tray, and therefore can take an impression with high accuracy.

2. Description of the Conventional Art

In a dental care, an impression material such as a silicone impression material or an alginate impression material is used for taking an impression within an oral cavity as a preparation stage of producing a prosthetic appliance. For inserting and retaining such an impression material within the oral cavity, an impression tray is used. In the impression taking, the impression material is loaded in the impression tray so as to be inserted into the oral cavity of a patient, the impression material is pressed into the oral cavity of the patient to be carried out the impression taking, the impression material is set, and the impression material is thereafter taken out of the oral cavity of the patient integrally in a state in which the set impression material is retained in the impression tray.

Large force is necessary at a time of taking out the set impression material from the oral cavity. As a result, there is a problem that the set impression material floats upward from the impression tray and is peeled off from the impression tray, so that an air gap is generated between the impression tray and the impression material. In the case that the air gap is generated, it is often the case that the impression material deforms from the initial set state, and a precision of the prepared dental prosthetic appliance is significantly lowered. Further, since the impression material has a property that the impression material is shrinked by a reaction and a volatilization of a water content after being set, the impression material is greatly affected by the shrinkage in the case that the impression material is peeled off from the impression tray, whereby a precision of the dental prosthetic appliance is further lowered. Accordingly, for the impression tray, there becomes important a performance that the impression material inserted into the oral cavity of the patient so as to be set can be taken out from the oral cavity of the patient without being deformed.

Generally, the impression tray is provided with a retention hole or a groove for mechanically retaining the set impression material. In other words, the impression material paste before being set enters into the retention hole and is set, whereby the set impression material and the tray are mechanically engaged. Particularly, since the set impression material tends to be peeled off in a peripheral portion of the tray, an application of forming an undercut portion (a rib) along the peripheral portion of the tray is carried out. However, since a sufficient amount of impression material cannot enter into the undercut portion, the peeling tends to be generated in the peripheral portion. Further, the impression tray is made of a metal or a plastic, and the metal tray can be easily formed an undercut portion having a height of 1.5 to 2.5 mm in the peripheral portion by processing as mentioned above. On the other hand, since the plastic tray is affected by a metal mold which is used for producing the tray and the molded tray cannot be taken out, the plastic tray cannot be formed an undercut portion having an effective height. Therefore, particularly in the impression tray made of a plastic, a problem that the peeling from the tray peripheral portion of the tray is large, and the deformation becomes larger occurs.

As the impression tray made of a plastic, there is a dental impression tray which is provided with a bottom wall, and inner and outer walls for forming an impression material retaining concave portion which is similar to a tooth row shape and is formed as a curved shape in a plan view, is provided with a handle portion which extends forward from side ends of front teeth in the bottom wall or the outer wall, and is provided at least in the inner and outer walls of the concave portion with a lot of impression material retention holes which inhibit a relative movement to the impression material over a whole surface (refer, for example, to Japanese Unexamined Patent Publication No. 2000-135227; hereinafter referred to as Patent Document 1). Patent Document 1 exemplifies a structure in which impression material retention holes provided in inner and outer opposed walls are elongated holes which are elongated shaped in a vertical direction and penetrate in an inward and outward direction of the concave portion (refer to claim 2), and the impression material retention hole provided in a front teeth side of the outer wall is provided in the bottom wall of the concave portion or the handle portion, or both of them and is communicated in a penetrating manner (refer to claim 3). However, Patent Document 1 shows only the structure in which a distance between the adjacent elongated holes in the drawing is very short in the impression material retention holes which are provided in the inner and outer opposed walls and elongated in the vertical direction as mentioned above, and any disclosure of a distance between the adjacent elongated holes and a width of the elongated hole does not exist in Patent Document 1. Further, an impression material retention hole having a circular cross sectional shape is provided in the bottom wall, however, a hole diameter and a distance between the adjacent impression material retention holes having the circular cross section shape are not disclosed at all. Further, the disclosed tray is provided only for taking a whole impression of the upper jaw and the lower jaw within the oral cavity, and there is not disclosed a structure for taking the impression of the local area within the oral cavity as a preparation stage of producing the partial denture, the bridge, the inlay or the like.

Therefore, it is unknown from Patent Document 1 mentioned above what dimension of the impression material retention holes can sufficiently retain the impression material. The impression material retention holes include the impression material retention holes which are provided in the inner and outer opposed walls and are elongated shaped in a vertical direction and the impression material retention holes which are provided in the bottom wall and have the circular cross section shape, in the tray for taking an impression of the local area within the oral cavity as the preparation stage of producing the partial denture, the bridge, the inlay or the like. Further, any means for removing a defect that the impression material in both ends of the tray tends to be peeled off does not exist.

SUMMARY OF THE INVENTION

Problem to be Solved by the Invention

An object of the present invention is to provide a plastic impression tray for a local area to be used for taking an impression of a local area within an oral cavity as a preparation stage of producing a partial denture, a bridge or an inlay as a prosthetic appliance in dentistry, wherein the impression tray can prevent a set impression material from floating upward from the tray and being peeled off from the tray, and therefore can take an impression with a high precision.

Means for Solving the Problem

The inventors of the present invention have devoted themselves to make a study for solving the problem mentioned above. As a result, the inventors have inquired into a fact that the problem mentioned above can be solved by forming a whole shape of the plastic impression tray for a local area as a shape having an outer wall which is provided upright from an outer side of a curve of a bottom portion formed as a gentle curved shape similar to an alveolar ridge shape and forming a approximately flat surface with an approximately uniform width at a corresponding length to at least three continuous teeth of a patient and is reduced its height gradually in one end side so as to come to the same height as the height of the bottom portion, and an inner wall which is provided upright from an inner side of the curve of the bottom portion via a circular arc shaped portion while being inclined to a direction that an upper end comes away from the bottom portion, and is reduced its height gradually in both end sides so as to come to the same height as the height of the bottom portion, setting a rim having a height of 0.01 to 1 mm in the bottom portion side along each of upper ends of the outer wall and the inner wall, forming elongated through holes each of which reaches the bottom portion from a portion just below the rim and has a width of 1.5 to 4.0 mm in the outer wall and the inner wall at approximately uniform distances in such a manner that a distance between the adjacent through holes is from 2 to 5 times the width of the through hole, and forming circular through holes each having a diameter of 3 to 6 mm in the bottom portion at the center of the distances of the adjacent elongated through holes which are provided in the outer wall and the inner wall, and setting an elongated end portion side through holes each of which has a width of 1.0 to 3.0 mm and a length of 5 to 15 mm and vertically to an axial direction of the curve of the bottom portion, in a side which is closer to an end portion than a line which connects the bottom portion side end portions of the respective elongated through holes positioned in the closest side to the end portions of the outer wall and the inner wall in both ends of the bottom portion, and the inventors have completed the present invention.

In the structure mentioned above, the inventors have inquired into a fact that it is preferable that the width of the elongated through holes which are provided in the outer wall and the inner wall is from 2.0 to 3.0 mm, the length is from 2 to 3 times the width, the distance between the elongated through holes which are provided in the outer wall and the inner wall is from 3 to 18 mm, the height of the rim is from 1 to 0.3 mm, and a rim having a height of 0.01 to 1 mm is provided in an opposite side to the bottom portion along each of the upper ends of the outer wall and the inner wall.

In other words, according to the present invention, there is provided a plastic impression tray for a local area, the impression tray having an outer wall which is provided upright from an outer side of a curve of a bottom portion formed as a gentle curved shape similar to an alveolar ridge shape and forming a approximately flat surface with an approximately uniform width at a corresponding length to at least three continuous teeth of a patient and is reduced its height gradually in one end side so as to come to the same height as the height of the bottom portion, and an inner wall which is provided upright from an inner side of the curve of the bottom portion via a circular arc shaped portion while being inclined to a direction that an upper end comes away from the bottom portion, and is reduced its height gradually in both end sides so as to come to the same height as the height of the bottom portion, wherein a rim having a height of 0.01 to 1 mm is provided in the bottom portion side along each of upper ends of the outer wall and the inner wall, elongated through holes each of which reaches the bottom portion from a portion just below the rim having a width of 1.5 to 4.0 mm are formed at approximately uniform distances in the outer wall and the inner wall in such a manner that a distance between the adjacent through holes is from 2 to 5 times the width of the through hole, circular through holes each having a diameter of 3 to 6 mm are formed in the bottom portion at the center of the distances of the adjacent elongated through holes which are provided in the outer wall and the inner wall, and elongated end portion side through holes each of which has a width of 1.0 to 3.0 mm and a length of 5 to 15 mm, are provided vertically to an axial direction of the curve of the bottom portion, in a side which is closer to an end portion than a line which connects the bottom portion side end portions of the respective elongated through holes positioned in the closest side to the end portions of the outer wall and the inner wall in both ends of the bottom portion. In the impression tray for a local area, it is preferable that the width of the elongated through holes which are provided in the outer wall and the inner wall is from 2.0 to 3.0 mm, the length is from 2 to 3 times the width, the distance between the elongated through holes which are provided in the outer wall and the inner wall is from 3 to 18 mm, the height of the rim is from 1 to 0.3 mm, and a rim having a height of 0.01 to 1 mm is provided in an opposite side to the bottom portion along each of the upper ends of the outer wall and the inner wall.

EFFECT OF THE INVENTION

Since the impression tray for a local area according to the present invention is formed as the shape having the outer wall which is provided upright from the outer side of the curve of the bottom portion formed as the gentle curved shape similar to the alveolar ridge shape and forming the approximately flat surface with the approximately uniform width at the corresponding length to at least three continuous teeth of the patient and is reduced its height gradually in the one end side so as to come to the same height as the height of the bottom portion, and the inner wall which is provided upright from the inner side of the curve of the bottom portion via the circular arc shaped portion while being inclined to the direction that the upper end comes away from the bottom portion, and is reduced its height gradually in the both end sides so as to come to the same height as the height of the bottom portion, and is made of a plastic, and the impression tray for a local area is provided with the rim having the height of 0.01 to 1 mm, preferably from 0.1 to 0.3 mm, is provided in the bottom portion side along each of the upper ends of the outer wall and the inner wall, the portion below the rim comes to an undercut portion, so that the set impression material is hard to float upward and be peeled off from the tray. Further, since the height of the rim is from 0.01 to 1 mm and is low, the rim does not form an obstacle to unloading from a metal mold at a time of an injection molding. Further, since the through holes each of which reaches the bottom portion from the portion just below the rim and is formed as the elongated hole having the width of 1.5 to 4.0 mm are formed approximately at the uniform distances in the outer wall and the inner wall in such a manner that the distance between the adjacent through holes is from 2 to 5 times the width of the through hole, the impression material appropriately enters into the through holes at a time of loading the silicone impression material or the alginate impression material within the tray so as to press to the desired position within the oral cavity of the patient, thereby taking the impression, and retains the set impression material, so that the set impression material is hard to float upward and be peeled off from the tray. Further, since the circular through holes each having the diameter of 3 to 6 mm are formed in said bottom portion at the center of the distances of the adjacent elongated through holes which are provided in the outer wall and the inner wall, the impression material enters into the circular through holes so as to retain the set impression material at a time of loading the silicone impression material or the alginate impression material within the tray so as to press to the desired position within the oral cavity of the patient, thereby taking the impression. However, since the circular through holes do not exist on the line connecting the elongated through holes which are provided in the outer wall and the inner wall, the impression material loaded in the same portion within the tray is not simultaneously pushed out to an outer side of the tray from the elongated through holes which are provided in the outer wall and the inner wall and the circular through holes which are provided in the bottom portion, and any space is not generated in the set impression material. Further, since the elongated end portion side through holes each of which has the width of 1.0 to 3.0 mm and the length of 5 to 15 mm, are provided vertically to the axial direction of the curve of the bottom portion, in the side which is closer to the end portion than the line which connects the bottom portion side end portions of the respective elongated through holes positioned in the closest side to the end portions of the outer wall and the inner wall in the both ends of the bottom portion, the impression material loaded within the tray enters into the elongated end portion side through holes which are provided in the both end portions of the bottom portion so as to be firmly retained. Therefore, there is not generated the defect that the impression material in the both end portions of the bottom portion tends to be peeled off.

Further, in the impression tray for a local area mentioned above, in the case that the width of the elongated through holes which are provided in the outer wall and the inner wall is from 2.0 to 3.0 mm, the length thereof is from 2 to 3 times the width, and the distance between the elongated through holes which are provided in the outer wall and the inner wall is from 3 to 18 mm, the impression material is better retained by the elongated through holes at a time of impression taking, and the set impression material is hard to float upward and be peeled off from the tray. Further, in the case that the rim having the height of 0.01 to 1 mm is provided in the opposite side to the bottom portion along each of the upper ends of the outer wall and the inner wall, a thickness of each of the upper ends of the outer wall and the inner wall is increased and a strength thereof is improved. However, the increase of the thickness does not form an obstacle to unloading from the metal mold at a time of the injection molding.

BRIEF EXPLANATION OF THE DRAWINGS

FIG. 5 is a perspective view of the impression tray for a local area shown in FIG. 1.

Figure 1:
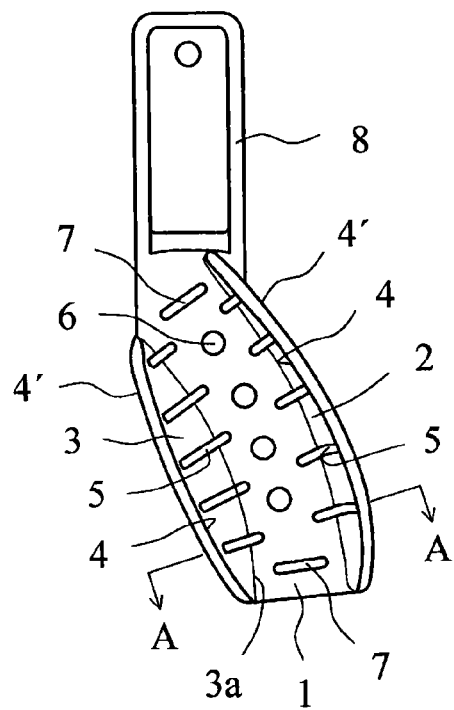
FIG. 1 is a plan view of an embodiment of an impression tray for a local area according to the present invention.
Figure 2:
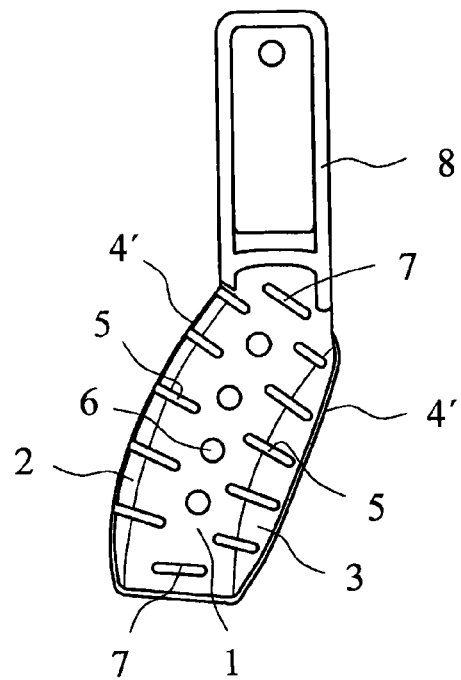
FIG. 2 is a back elevational view of the impression tray for a local area shown in FIG. 1.
Figure 3:
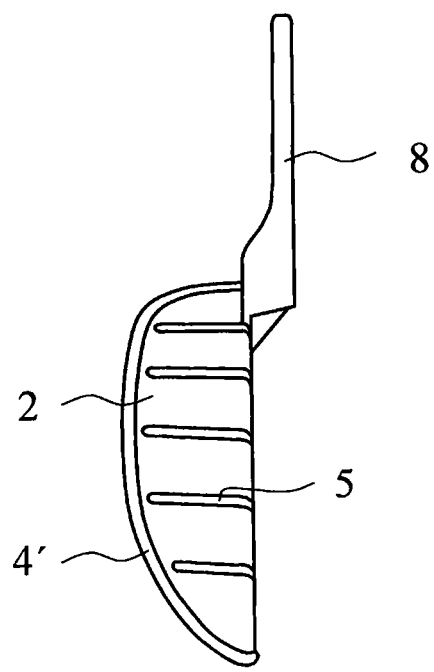
FIG. 3 is a right side elevational view of the impression tray for a local area shown in FIG. 1.
Figure 4:
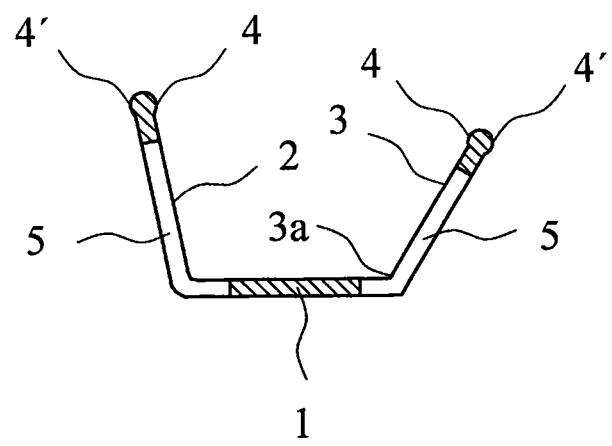
FIG. 4 is an enlarged end elevational view along a line A-A in FIG. 1.

DESCRIPTION OF REFERENCE NUMERALS 1 bottom portion
2 outer wall
3 inner wall
3a circular arc shaped portion
4 rim
4' rim
5 elongated through hole
6 circular through hole
7 elongated end portion side through hole
8 handle portion

DETAILED DESCRIPTION OF PREFERRED EMBODIMENT

An impression tray for a local area according to the present invention is a plastic impression tray for a local area, the impression tray having a bottom portion 1 which is formed as a gentle curve shape similar to an alveolar ridge shape and forms a approximately flat surface with an approximately uniform width at least at a corresponding length to three contiguous teeth of a patient, an outer wall 2 which is provided upright from an outer side of the curve of the bottom portion 1 and is reduced its height gradually in one end side so as to have the same height as the bottom portion 1, and an inner wall 3 which is provided upright from an inner side of the curve of the bottom portion 1 in the same manner via a circular arc shaped portion 3a while being inclined to a direction that an upper end comes away from the bottom portion 1 and is reduced its height gradually in both end sides so as to come to the same height as the bottom portion 1. Further, a rim 4 having a height of 0.01 to 1 mm, preferably from 0.1 to 0.3 mm is provided in a side of the bottom portion 1 along each of upper ends of the outer wall 2 and the inner wall 3. The rim 4 is provided for forming an undercut portion below the rim 4 so as to generate an effect of preventing a set impression material from floating upward and being peeled off from the tray. If the height of the rim 4 is less than 0.01 mm, an effect of forming the undercut portion cannot be expected, and if the height goes beyond 1 mm, the rim forms an obstacle to unloading from a metal mold at a time of injection molding of the tray due to its excessive height and it is impossible to well carry out the injection molding. Further, in the case the a rim 4' having a height of 0.01 to 1 mm is further provided in an opposite side to the bottom portion 1 along each of the upper ends of the outer wall 2 and the inner wall 3, a thickness of each of the upper ends of the outer wall 2 and the inner wall 3 is increased and a strength thereof is improved. However, the rim 4' does not form an obstacle to unloading from the metal mold at a time of the injection molding and is preferably provided.

Reference numeral 5 denotes a elongated through hole which is provided in the outer wall 2 and the inner wall 3, and has a width of 1.5 to 4.0 mm reaching the bottom portion 1 from a portion just below the rim 4. The through hole 5 is formed such that a distance between the adjacent through holes 5 is approximately equal to 2 to 5 times the a width of the through hole 5. If the width of the elongated through hole 5 is less than 1.5 mm, the impression material does not appropriately enter into the through holes 5 at a time of loading a silicone impression material or an alginate impression material in the tray and pressing to a desired position within an oral cavity of a patient so as to take an impression, and a phenomenon that the set impression material cannot be retained and falls off is generated. Accordingly, this width is not preferable. If the width goes beyond 4.0 mm, a pressure is not sufficient only by loading the silicone impression material or the alginate impression material in the tray and pressing to the desired position within the oral cavity of the patient. Accordingly, it is impossible to accurately take the impression, therefore this width is not preferable. Further, if the distance between the through hole 5 and the adjacent through hole 5 is less than twice the width of the through hole 5, the adjacent through holes 5 come too close to each other. Therefore, the pressure is not sufficient at a time of loading the silicone impression material or the alginate impression material in the tray and pressing to the desired position within the oral cavity of the patient so as to take the impression. Therefore, it is impossible to accurately take the impression. Further, if the distance goes beyond fivefold, the adjacent through holes 5 are too away from each other. Therefore, there is not generated the effect that the impression material sufficiently enters into the through holes 5 so as to be retained at a time of loading the silicone impression material or the alginate impression material in the tray and pressing to the desired position within the oral cavity of the patient so as to take the impression. Accordingly, this distance is not preferable. It is particularly preferable that the width of the elongated through hole 5 is from 2.0 to 3.0 mm, the length of the through hole 5 is from 2 to 3 times the width, and the distance between the adjacent through holes 5 is from 3 to 18 mm.

Reference numeral 6 denotes a circular through hole which is formed in the bottom portion 1 positioned at the center of the distances of the adjacent elongated through holes 5 provided in the outer wall 2 and the inner wall 3 and has a diameter of 3 to 6 mm. It is necessary for the circular through hole 6 to be formed in the bottom portion 1 which is positioned at the center of the distances of the adjacent elongated through holes 5 provided in the outer wall 2 and the inner wall 3 because the impression material loaded in the same position within the tray simultaneously enters into the elongated through holes 5 and the circular through holes 6 and is pushed out of the tray at a time of loading the silicone impression material or the alginate impression material in the tray and pressing to the desired position within the oral cavity of the patient so as to take the impression, whereby a space is generated in the set impression material, and a phenomenon that the impression material is not closely attached to the desired position within the oral cavity of the patient is generated, so that there is a possibility that a good impression taking cannot be carried out. If the diameter of the circular through hole 6 is less than 3 mm, there is not generated the effect that the impression material sufficiently enters into the circular through holes 6 so as to be retained at a time of loading the silicone impression material or the alginate impression material in the tray and pressing to the desired position within the oral cavity of the patient so as to take the impression. Accordingly, this diameter is not preferable. If the diameter goes beyond 6 mm, the impression material enters into the circular through holes 6 too much, and the phenomenon that the impression material is not closely attached to the desired position within the oral cavity of the patient is generated, so that there is a possibility that the good impression taking cannot be carried out.

Reference numeral 7 denotes an elongated end portion side through hole which is provided in a closer side to an end portion than a line connecting end portions in the bottom portion side of the elongated through holes 5 positioned at the closest sides to the end portions in the outer wall 2 and the inner wall 3 in both ends of the bottom portion 1 vertically to an axial direction of a curve of the bottom portion 1, has a width of 1.0 to 3.0 mm and a length of 5 to 15 mm. Since the end portion side through holes 7 are provided, the impression material loaded in the tray enters into the elongated end portion side through holes 7 in the both end portions of the tray so as to be firmly retained, there is not generated the defect that the impression material in the both end portions tends to be peeled off. In the elongated end portion side through hole 7 provided for achieving the effect mentioned above, in the case that the width thereof is less than 1.0 mm, there is not generated the effect that the impression material sufficiently enters into the end portion side through holes 7 so as to be retained at a time of loading the silicone impression material or the alginate impression material in the tray and pressing to the desired position within the oral cavity of the patient so as to take the impression. Therefore, this width is not preferable. Further, if the width goes beyond 3.0 mm, the impression material enters into the end portion side through holes 7 too much. Accordingly, there is generated the phenomenon that the impression material in the both end portions of the bottom portion 1 is not closely attached to the desired position within the oral cavity of the patient, and there is a possibility that a good impression taking cannot be carried out.

Reference numeral 8 denotes a handle portion which is provided in the bottom surface of one end portion of the bottom portion 1. The handle portion may be fixed to the bottom portion 1 or may be structured such as to be detachably provided at a predetermined position of the bottom surface in the bottom portion 1 as described in Japanese Patent Application No. 2011-217753 which was proposed by the applicant of the present patent application.

In the impression tray for a local area according to the present invention mentioned above, in the case that the impression taking is carried out by loading the paste-like silicone impression material or alginate impression material on the bottom portion 1 between the outer wall 2 and the inner wall 3 and pressing to the desired position within the oral cavity of the patient, the impression material is expanded to the outer wall 2 side and the inner wall 3 side and comes into contact with the undercut portion below the rim 4. Accordingly, the impression material can be prevented from floating upward and being peeled off from the tray after being set. Further, the impression material appropriately enters into the elongated through holes 5 each of which reaches the bottom portion 1 from the portion just below the rim 4 in the outer wall 2 and the inner wall 3 and has the width of 1.5 to 4.0 mm, and into the circular through holes 6 each of which is formed in the bottom portion 1 positioned at the center of the distances of the adjacent elongated through holes 5 which are provided in the outer wall 2 and the inner wall 3 and has the diameter of 3 to 6 mm, and the set impression material is retained. The effect of retaining the set impression material mentioned above becomes higher in the case that the width of the elongated through hole 5 is from 2.0 to 3.0 mm and the length is from 2 to 3 times the width, and the case that the distance between the elongated through holes 5 is from 3 to 18 mm, and these cases are preferable.

Further, in the both end portions of the bottom portion 1, the impression material loaded in the tray enters into the elongated end portion side through holes 7 each of which is provided in the side closer to the end portion than the line connecting the bottom portion side end portions of the elongated through holes 5 which are positioned in the both end portions in the outer wall 2 and the inner wall 3 vertically to the axial direction of the curve of the bottom portion 1, has the width of 1.0 to 3.0 mm and the length of 5 to 15 mm, and the impression material is firmly retained. Therefore, there is not generated the defect that the impression material in the both end portions of the tray tends to be peeled off.

As mentioned above, in the impression tray for a local area according to the present invention, in addition to the effect of the undercut portion by the rim 4 which is provided in the bottom portion 1 side along each of the upper ends of the outer wall 2 and the inner wall 3, the impression material loaded in the tray enters into the elongated through holes 5 each of which reaches the bottom portion 1 from the portion just below the rim 4 in the outer wall 2 and the inner wall 3, is provided at the particular width and distance, into the circular through holes 6 each of which is formed in the bottom portion 1 positioned at the center of the distances of the adjacent elongated through holes 5 provided in the outer wall 2 and the inner wall 3 and has the particular diameter, and into the elongated end portion side through holes 7 each of which is provided in the side closer to the end portion than the line connecting the bottom portion side end portions of the elongated through holes 5 which are positioned at the both end portions in the outer wall 2 and the inner wall 3 vertically to the axial direction of the curve of the bottom portion 1, and the impression material is firmly retained. Therefore, since it is possible to prevent the set impression material from floating upward and being peeled off from the tray, it is possible to take the impression at a high precision.

What is claimed is:

1. An impression tray for a local area, comprising:
   a plastic tray having a bottom portion having a curved shape, an outer wall formed upright from an outer side of the curve of the bottom portion, and an inner wall formed upright from an inner side of the curve of the bottom portion via a circular arc shaped portion,
   wherein the bottom portion is configured to substantially fit a residual ridge of a patient, the bottom portion has a flat surface, a width of the bottom portion is substantially constant, a length of the bottom portion is substantially equal to a length of at least three continuous teeth of the patient, the bottom portion has a first end side and a second end side,
   the outer wall has a first end connected to the first end side of the bottom portion, and a second end, a height of the outer wall with respect to the bottom portion gradually decreases from the second end toward the first end such that an upper edge of the outer wall is sloped from the second end to the first end and that the first end of the outer wall merges the first end side of the bottom portion,
   the inner wall is inclined away from the bottom portion, the inner wall has a first end connected to the first end side of the bottom portion, and a second end connected to the second end side of the bottom portion, a height of the inner wall with respect to the bottom portion gradually decreases from a middle portion of the inner wall toward each of the first and second ends such that an upper edge of the inner wall is sloped from the middle portion toward each of the first and second ends and that the first end of the inner wall merges the first end side of the bottom portion and the second end of the inner wall merges the second end side of the bottom portion,
   each of the inner wall and the outer wall has an inside rim having a height of 0.01 to 1 mm along the upper edge on a side of the bottom portion, and a plurality of elongated holes penetrating through a respective one of the inner wall and the outer wall and reaching to the bottom portion from a portion just below the inside rim, each of the plurality of elongated holes has a width of 1.5 to 4.0 mm, the plurality of elongated holes of the respective one of the inner wall and the outer wall is arranged at substantially regular intervals and is formed such that a distance between adjacent elongated holes is from 2 to 5 times of the width of a single elongated hole,
   the bottom portion comprises a plurality of circular holes penetrating through the bottom portion, each having a diameter of 3 to 6 mm and being formed at the center of the distance between the adjacent elongated holes, and
   the bottom portion comprises a pair of elongated holes penetrating through the bottom portion, each having a width of 1.0 to 3.0 mm and a length of 5 to 15 mm, the pair of elongated holes being formed substantially perpendicular to an axial direction of the curve of the bottom portion, and each of the pair of elongated holes being closer to a respective one of the first and second end side of the bottom portion than the elongated holes of the outer wall and the inner wall.

2. The impression tray for a local area according to claim 1, wherein the width of a single elongated hole of the outer wall and the inner wall is from 2.0 to 3.0 mm, and
   a length of a single elongated hole of the outer wall and the inner wall is from 2 to 3 times of the width of the single elongated hole.

3. The impression tray for a local area according to claim 1, wherein the distance between the adjacent elongated holes of the respective one of the outer wall and the inner wall is from 3 to 18 mm.

4. The impression tray for a local area according to claim 1, wherein the height of the inside rim on the outer wall and the inner wall is from 0.1 to 0.3 mm.

5. The impression tray for a local area according to claim 1, wherein each of the outer wall and the inner wall further comprises an outside rim having a height of 0.01 to 1 mm along the upper edge on a side opposite to the bottom portion.

6. The impression tray for a local area according to claim 1, further comprising a handle portion connected to the second end side of the bottom portion.

7. The impression tray for a local area according to claim 6, wherein the handle portion is detachably connected to the second end side of the bottom portion.

* * * * *